_United States Patent_ [19]

Kramer et al.

[11] Patent Number: 5,217,896

[45] Date of Patent: Jun. 8, 1993

[54] MONOCLONAL ANTIBODIES RECOGNIZING PARATHYROID HORMONE-LIKE PROTEIN

[75] Inventors: Steven P. Kramer, Kew Gardens; David M. Valenzuela, Franklin Square; Frederick H. Reynolds, Jr., Syosset; John M. Sorvillo, Merrick, all of N.Y.

[73] Assignee: Oncogene Science, Inc., Uniondale, N.Y.

[21] Appl. No.: 292,263

[22] Filed: Dec. 30, 1988

[51] Int. Cl.$^5$ ............... C12N 5/20; C12N 15/02; C07K 15/28; C12P 21/08

[52] U.S. Cl. ............... 435/240.27; 530/388.24; 530/391.1; 530/391.3; 435/70.21; 435/172.2

[58] Field of Search ........... 530/387, 389, 413, 388.24, 530/391.1, 391.3; 435/240.27, 70.21, 172.2

[56] References Cited

PUBLICATIONS

Mangin, M. et al., (1988) Proc. Natl. Acad. Sci. USA 85: 597.
Burtis, W. J. et al., (1987) J. Biol. Chem. 262:7157.
Moseley, J. M. et al., (1987) Proc. Natl. Acad. Sci. USA 84: 5048.
Nissenson, R. A. et al., (1988) J. Biol. Chem. 263: 12866.
Suva, L. J. et al., (1987) Science 237: 893.
Weir et al. Endocrinology 123(6):2744-2751 1988.
Maurer et al. Methods in Enzymology vol. 70 pp. 49-70, 1980.
Morrison, Science 229:1202-1207, 1985.
Buck et al. in Kennett et al Eds. _Monoclonal Antibodies and Functional Cell Lines_ Plenum Press, 1984.

_Primary Examiner_—John J. Doll
_Assistant Examiner_—Paula Hutzell
_Attorney, Agent, or Firm_—John P. White; Robert J. Cobert

[57] ABSTRACT

This invention provides a monoclonal antibody which specifically forms a complex with amino acids 1-87 of PTHLP which does not form a complex with amino acids 1-34 of PTHLP, and which forms a complex with the epitope to which any of the monoclonal antibodies produced by the hybridomas 212-10.7, (ATCC Accession No. HB9930), 199-999 (ATCC Accession No. HB9929), 199-278 (ATCC Accession No. HB9931), is directed.

This invention further provides methods of detecting PTHLP and of diagnosing and treating humoral hypercalcemia of malignancy.

15 Claims, 7 Drawing Sheets

FIGURE 1A

Segment A

BamH I      Nde I      [1]

```
            M   A   V   S   E   H   Q   L   L   H   D
GATCCAACAT ATG GCG GTG AGC GAA CAC CAG CTG CTG CAC GAT
    GTTGTA TAC CGC CGC TCG CTT GTG GTC GAC GAC GTG CTA
```

[2]

```
 K   G   K   S   I   Q   D   L      Sal I
AAA GGC AAA AGC ATC CAA GAT CTG CG
TTT CCG TTT TCG TAG GTT CTA GAC GCAGCT
```

Segment B

BamH I   Sal I      [3]

```
        R   R   R   F   F   L   H   H   L   I   A   E
GATCC CGT CGA CGT TTC TTC CTG CAC CAC CTG ATT GCG GAA
    G GCA GCT GCA AAG AAG GAC GTG GTG GACTAA CGC CTT
```

[4]

```
 I   H   T   A   E   I   R   A   T   S   E   V   S
ATC CAC ACC GCG GAA ATC CGT GCG ACC AGC GAA GTG AGC
TAG GTG TGG CGC CTT TAG GCA CGC TGG TCG CTT CAC TCG
```

EcoR I      [5]

```
 P   N   S   K   P   S   P   N   T   K   N   H   P
CCG AAT TCT AAA CCG TCC CCA AAT ACC AAA AAC CAC CCG
GGC TTA AGA TTT GGC AGG GGT TTA TGG TTT TTG GTG GGC
```

[6]      KpN I

```
 V   R   F   G   S   D   D   E   G   R   Y   L   T
GTG CGT TTC GGC AGC GAT GAT GAA GCC CGG TAC CTG ACC
CAC GCA AAG CCG TCG CTA CTA CTT CGG GCC ATG GAC TGG
```

[7]

```
 Q   E   T   N   K   V   E   T   Y   K   E   Q   P
CAG GAA ACC AAC AAA GTG GAA ACC TAC AAA GAA CAG CCG
GTC CTT TGG TTG TTT CAC CTT TGG ATG TTT CTT GTC GGC
```

Sma I      [8]    Hind III

```
 L   K   T   P   G
CTG AAA ACC CCG GGC A TCTAGA
GAC TTT TGG GGC CCG T AGATCTTCGA
```

FIGURE 1A (cont.)

Segment C

BamH I     Sma I              [9]

```
        P   G   K   K   K   G   K   P   G   K   R
GATCC CCG GGC AAA AAG AAG AAA GGC AAA CCG GGC AAA CGT
    G GGC CGG TTT TTC TTC TTT CCG TTT GGC CCG TTT GCA
```

[10]
```
K   E   Q   E   K   K   K   R   R   T   R   S   A   W
AAA GAA CAG GAA AAG AAG AAA CGT CGT ACC CGT AGC GCG TGG
TTT CTT GTC CTT TTC TTC TTT GCA GCA TGG GCA TCG CGC ACC
```

[11]
```
L   D   S   G   V   T   G   S   G   L   E   G   D   H
CTG GAT AGC GGC GTG ACC GGC AGC GGC CTG GAA GGC GAT CAC
GAC CTA TCG CCG CAC TGG CCG TCG CCG GAC CTT CCG CTA GTG
```

[12]
```
L   S   D   T   S   T   T   S   L   E   L   D   S   R
CTG AGC GAT ACC AGC ACC ACC AGC CTG GAA CTG GAT AGC CGT
GAC TCG CTA TGG TCG TGG TGG TCG GAC CTT GAC CTA TCG GCA
```

Sal I
```
R   H   X
CGT CAC TGATCTAGAG
GCA GTG ACTAGATCTCAGCT
```

MONOCLONAL ANTIBODIES RECOGNIZING PARATHYROID HORMONE-LIKE PROTEIN

BACKGROUND OF THE INVENTION

Throughout this application, various publications are referenced by Arabic numerals within parentheses. Full citations for these publications may be found at the end of the specification immediately preceding the claims. The disclosures of these publications in their entireties are hereby incorporated by reference into this application in order to more fully describe the state of the art as known to those skilled therein.

Malignancy associated hypercalcemia condition (MAHC) was first described in a patient with a renal carcinoma who had a single bone metastases and developed hypercalcemia and hypophosphatemia (1). It was noted that bone resorption could not readily account for hypophosphatemia and suggested that the tumor might be secreting a humoral factor similar to parathyroid hormone (PTH), with skeletal and renal actions which would produce hypophosphatemia and hypercalcemia. The hypothesis that MAHC could have a humoral basis was supported by the observation that in certain patients without bone metastases, hypercalcemia could be cured by resection of the primary tumor which was distant from the bone (2,3). These patients characteristically have squamous, renal, bladder or ovarian carcinomas and have little or no evidence of skeletal disease.

More detailed clinical evaluations of patients with MAHC (4-6) have indicated that such patients fall into two groups. One group has suppressed nephrogenous cAMP (NcAMP) levels and the other has elevated levels. The former group of patients most commonly have malignancies of the breast or hematologic malignancies in addition to widespread bone metastases suggesting that MAHC may be due to the interaction between the metastases and bone, in this case.

The latter group of patients (elevated NcAMP) exhibit a number of common features including:
1. predominantly renal or squamous carcinomas;
2. few or no bone metastases;
3. significantly elevated excretion of calcium relative to patients with primary hyperparathyroidism;
4. low levels of circulating 1,25-dihydroxyvitamin D [$1,25(OH)_2$ D];
5. reduced or undetectable levels of circulating immunoreactive parathyroid hormone (PTH); and
6. hypophosphatemia and depressed renal phosphorous thresh hold.

These symptoms indicate a humoral basis for MAHC observed among this group of patients and are presently used to define the syndrome termed humoral hypercalcemia of malignancy (HHM).

Biochemical analyses of tumor extracts from patients with HHM led to the identification of a polypeptide factor capable of stimulating receptor-linked enzymatic activities which are also stimulated by parathyroid hormone (PTH) (7). Purification and N-terminal sequence analysis of this PTH-like protein (PTHLP) revealed a high degree of homology to PTH near the amino-terminus (8 out 13 amino acids) but no homology beyond position 13 (8,9). During the same period of time similar factors were identified in conditioned media from cultured cells derived from patients with HHM, renal carcinomas, a lung carcinoma, and more recently, from an HTLV-1 infected T-cell line (10-17). Purification and amino-terminal sequence analyses of these factors (14,17) indicated amino-termini identical to that of PTHLP purified directly from tumors of HHM patients.

Using oligonucleotide probes based upon the amino-terminal amino acid sequence to screen human cDNA libraries, two cDNA sequences have been obtained encoding identical polypeptides containing a 36 amino acid leader sequence and a 141 amino acid mature protein (18,19). Using similar techniques and a probe based upon the reported cDNA sequence, a third cDNA was obtained which was identical except at the extreme 3' end, where alternative RNA splicing led to an mRNA encoding a 139 amino acid mature protein (20). These results are in agreement with those of others (21) who have also observed only a single copy of the PTHLP gene but 3 different mRNAs, arising from 3 alternative 3'-region splices, encoding mature polypeptides of 139, 141, and 161 amino acids.

Since the determination of the amino acid sequence of PTHLP there have been numerous reports describing the in vitro and in vivo biological activities of synthetic amino-terminal peptides of PTHLP corresponding to the receptor binding and biologically active region of PTH (22-27). The results of these studies indicate that these peptides have the following biological activities:
1. stimulate the PTH-receptor linked adenylate cyclase in canine renal cortex membranes;
2. stimulate the PTH-receptor linked adenylate cyclase in rat osteosarcoma cells;
3. bind the PTH-receptor in various tissues with equal affinity as PTH although the efficiency of coupling to adenylate cyclase, and hence the PTHLP stimulated activity relative to the PTH stimulated activity, differs in membranes from different sources;
4. stimulate the resorption of calcium from cultured rat fetal long bones;
5. induce in vivo hypercalcemia when infused into rats or injected into mice;
6. stimulate in vivo 1,25-dihydroxy vitamin $D_3$ formation when infused into rats;
7. stimulate the excretion of cAMP and phosphorous from perfused rat kidneys; and
8. stimulate migration of rat osteoclasts to cortical and trabecular bone surfaces with equal potency to that of bovine (b) PTH(1-34).

These activities are expected for a putative factor responsible for HHM. Furthermore, the cloning and expression in bacteria of full length (141 amino acids) PTHLP has recently been accomplished (28). Although the polypeptide was not purified to homogeneity, activity measurements suggested a similar ability to stimulate adenylate cyclase as that of synthetic PTHLP(1-34) (28).

It is not yet clear how the similarities and differences in activities of PTHLP and PTH reflect upon the physiological and pathophysiological role of PTHLP in the regulation of calcium homeostasis. In addition, the importance of sequence differences in the carboxyl-terminal region of mature PTHLP polypeptides resulting from alternative splicing of mRNA has not yet been addressed. One reason for this is that there is no method available for adequate differentiation between PTH and PTHLP in crude systems such as tissue and tumor extracts or blood. An immunological assay would overcome the inherent ambiguity of biological assays by avoiding the involvement of a hormone receptor recognizing both PTH and PTHLP. One type of immuoassay has been reported (29) which involves a rabbit polyclonal antisera recognizing a synthetic amino-terminal peptide of PTHLP. This assay is subject to adverse effects from serum and thus requires an extraction procedure before samples can be tested. Since the circulating form(s) of PTHLP are not known and the physiochemical properties of larger PTHLP species are substantially different than those of the amino-terminal peptide, the extraction procedures currently in use are not likely to yield the correct amounts of PTHLP. Thus, results obtained with this assay have not indicated significant elevation of levels of PTHLP in MAHC patients.

To overcome these problems high affinity monoclonal and polyclonal antibodies which are extremely specific for PTHLP need to be developed. The claims and methods provided below pertain to antibodies with these properties.

SUMMARY OF THE INVENTION

This invention provides a monoclonal antibody which specifically forms a complex with amino acids 1-87 of PTHLP, which does not form a complex with amino acids 1-34 of PTHLP, and which forms a complex with the epitope to which any of the monoclonal antibodies produced by the hybridomas 212-10.7 (ATCC Accession No. HB9930), 199-999 (ATCC Accession No. HB9929), and 199-278 (ATCC Accession No. HB9931) is directed. The invention further provides methods of detecting PTHLP and of diagnosing and treating humoral hypercalcemia of malignancy.

1A. Oligonucleotides were annealed to produce the indicated fragments, which were later assembled to obtain complete or partial sequences of the PTHLP gene. Segment "a" corresponds to a 69 base pair (bp) BamHI-SalI fragment encoding the first 18 amino acids of PTHLP with an additional methionine residue prior to residue 1. Segment "b" corresponds to a 195 bp BamHI-HindIII fragment encoding amino acids 19 to 87. Segment "c" corresponds to a 183 bp BamHI-HindIII fragment encoding amino acids 86-141.

Segment b alone, or after ligation to segment a, was cloned into vector pTZ19R to produce plasmid pTZ19R(b) or pTZ19R(ab), respectively. Segment c was cloned separately into pTZ19R to produce pTZ19R(c).

1B. The complete gene or partial sequences of PTHLP were expressed as fusion proteins with the trpE gene product in vector pATH-1 or PATH-3. Fragment B was released from pTZ19R(b) by digestion with BamHI and SalI and cloned into the same restricion sites in pATH-3. Fragment ab was obtained from pTZ19R(ab) after digestion with BamHI and HindIII and cloned into the BamHI-HindIII sites of pATH-1. The complete sequence of PTHLP was obtained by ligation of fragment ab, obtained from pTZ19R(ab digested with BamHI and SmaI, and fragment c, obtained from pTZ19R(c) digested with SDmaI and SalI, into BamHI-SalI sites of vector pATH-1. The complete PTHLP coding sequence is fused to the trpE gene at base 1014 (31). Encoded methionine residies are indicated by arrows. B: BamHI; C: ClaI; E: EcoRI; H: HindIII; P: PstI; S: SalI; Sc: SacI: Sm: SmaI; X: XbaI.

Figure 2:
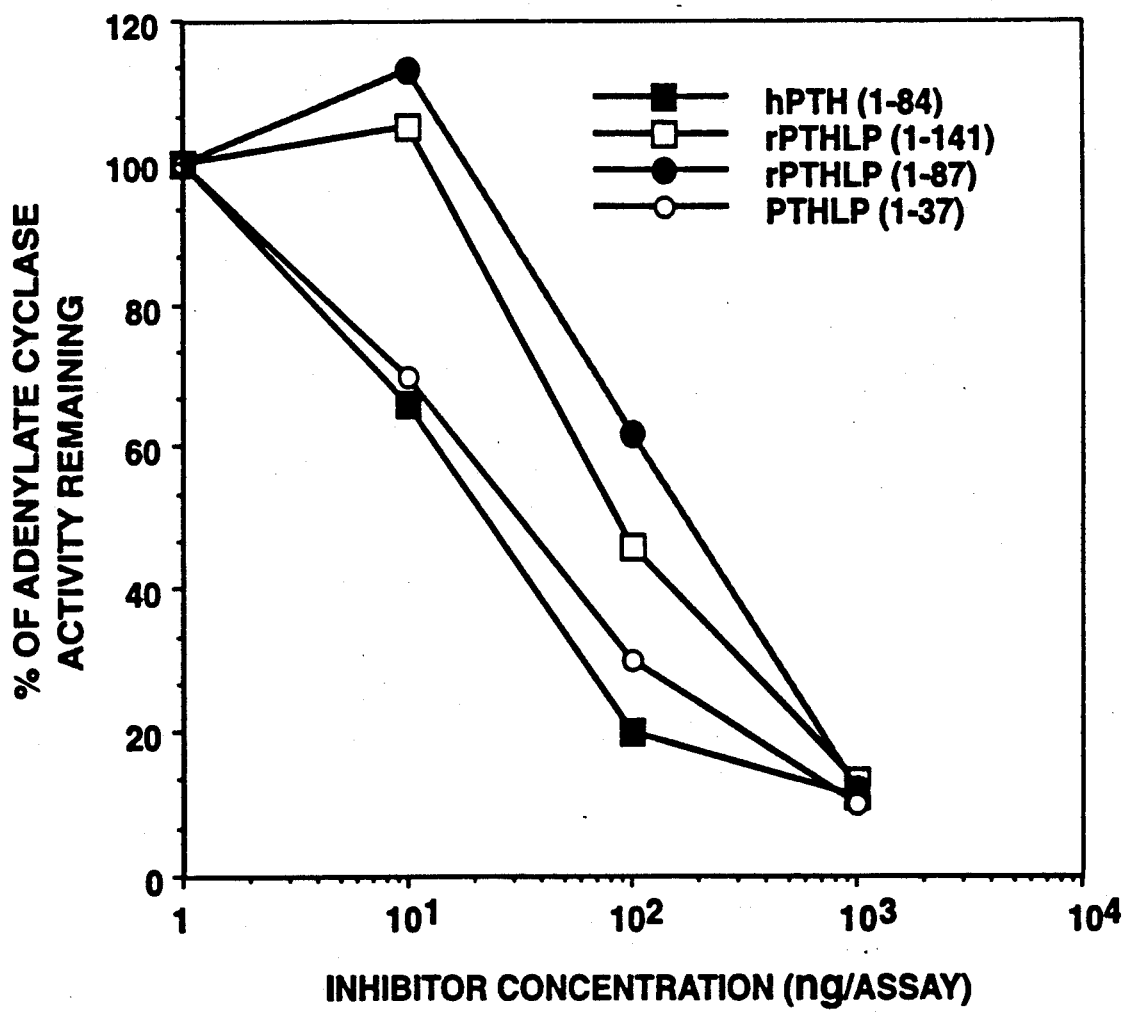

FIG. 2: Inhibition of rPTHLP bioactivity by [Nle$^{8,18}$, Tyr$^{34}$]-bPTH(3-34)amide. Assay conditions for the canine renal membrane adenylate cyclase assay were as described under Methods except that the indicated concentrations of the competitive inhibitor [Nle$^{8,18}$, Tyr$^{34}$-bPTH(3-34)amide were included in the assay mixture. 100% activity remaining was defined as the activity in the absence of inhibitor.

Figure 3:
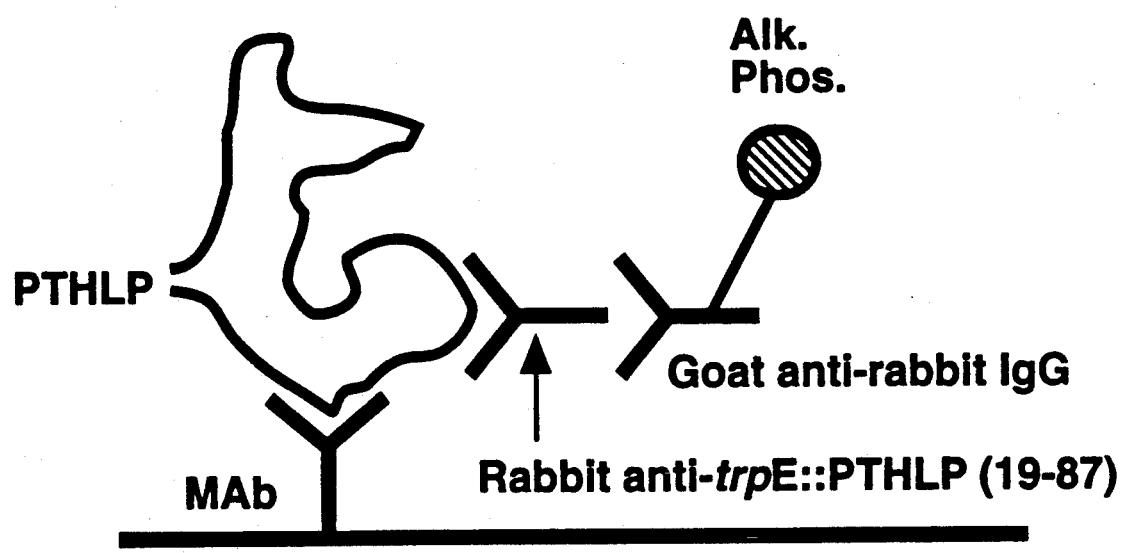

FIG. 3: Two-site immunometric assay for PTHLP. The diagram shown reflects the protocol described under Methods.

Figure 4:
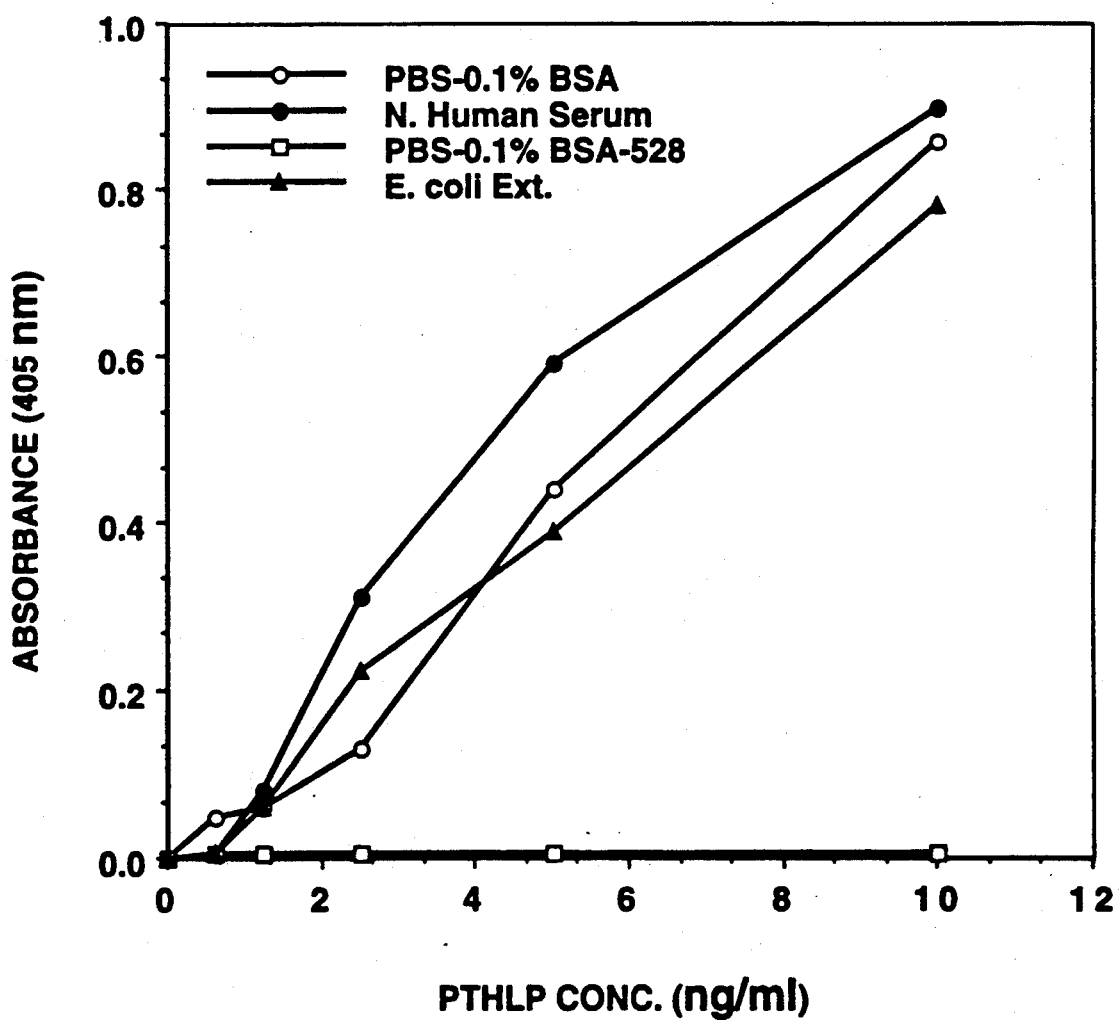

FIG. 4: Standard curves for the two-site immunometric assay. The assay was performed as described under Methods except that the diluent used during incubation with PTHLP(1-87) was as labeled above. The curve labeled PBS-0.1%BSA, 528 was obtained using monoclonal antibody 528 for capture instead of monoclonal antibody 212-10.7.

Figure 5:
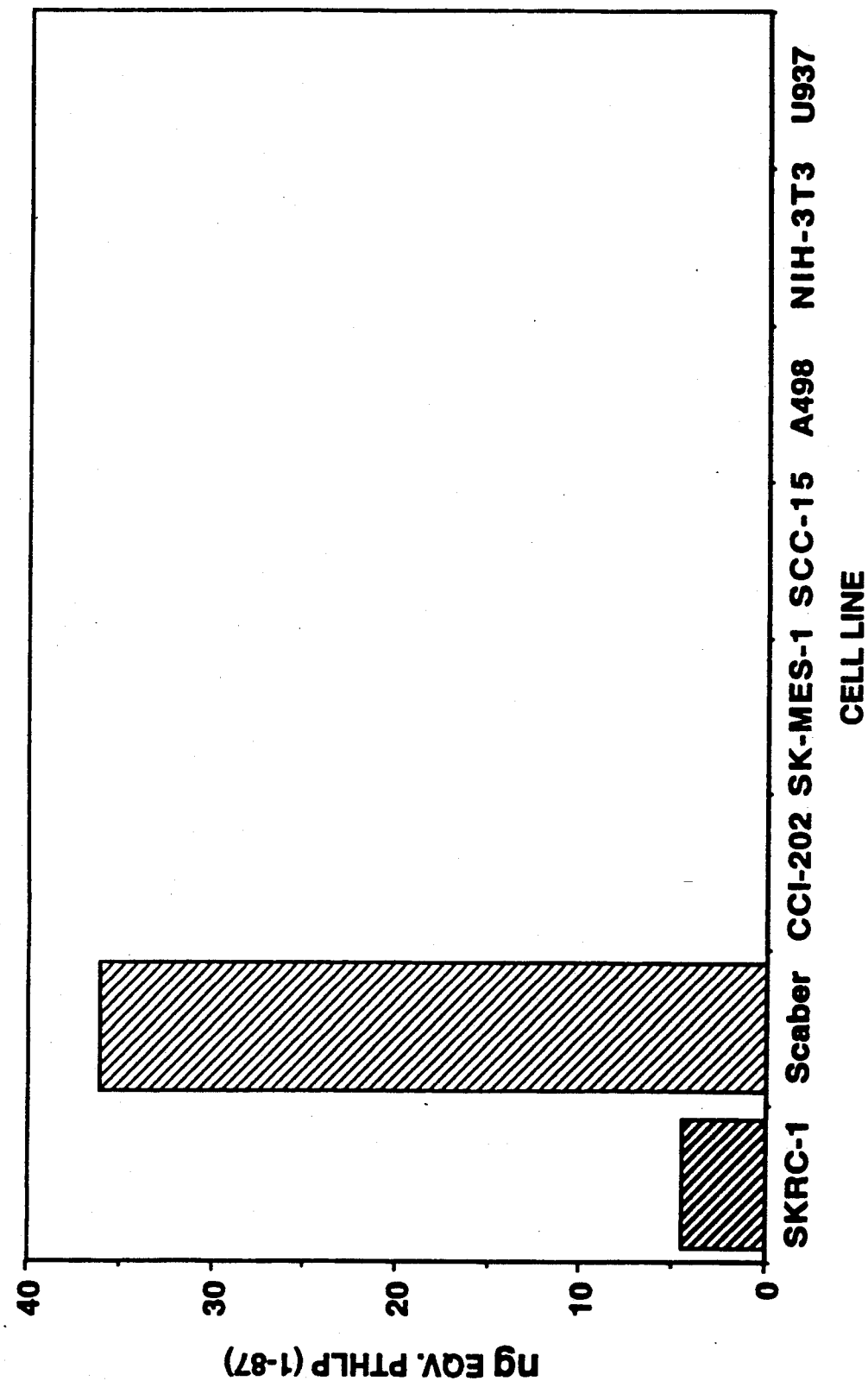

FIG. 5: PTHLP levels in conditioned media. The two-site immunometric assay was used to determined PTHLP imunoreactivity in conditioned media of the cultured cell lines shown. The values were quantitated by comparison to a standard curve obtained with PTHLP(1-87).

DETAILED DESCRIPTION OF THE INVENTION

The present invention provides a monoclonal antibody which specifically forms a complex with amino acids 1-87 of PTHLP, which does not specifically form a complex with amino acids 1-34 of PTHLP, and which forms a complex with the epitope to which any of the monoclonal antibodies produced by the hybridomas 212-10.7, (ATCC Accession No. HB9930) 199-999 (ATCC Accession No. HB9929) and 199-278 (ATCC Accession No. HB9931) is directed.

In one embodiment the invention provides a mouse monoclonal antibody which specifically forms a complex with amino acids 1-87 of PTHLP, which does not specifically form a complex with amino acids 1-34 of PTHLP, and which forms a complex with the epitope to which any of the monoclonal antibodies produced by the hybridomas 212-10.7, (ATCC Accession No. HB9930) 199-999 (ATCC Accession No. HB9929) and 199-278 (ATCC Accession No. HB9931) is directed. In another embodiment this invention provides a human monoclonal antibody which specifically forms a complex with amino acids 1-87 of PTHLP, which does not specifically form a complex with amino acids 1-34 of PTHLP, and which forms a complex with the epitope to which any of the monoclonal antibodies produced by the hybridomas 212-10.7, (ATCC Accession No. HB9930) 199-999 (ATCC Accession No. HB9929) and 199-278 (ATCC Accession No. HB9931) is directed. In yet another embodiment this invention provides a chimeric monoclonal antibody which specifically forms a complex with amino acids 1-87 of PTHLP, which does not specifically form a complex with amino acids 1-34 of PTHLP, and which forms a complex with the epitope to which any of the monoclonal antibodies produced by the hybridomas 212-10.7, (ATCC Accession No. HB9930) 199-999 (ATCC Accession No. HB9929) and 199-278 (ATCC Accession No. HB9931) is directed. Additionally, in a presently preferred embodiment of the invention, the monoclonal antibody specifically forms a complex with amino acids 19-87 of PTHLP.

In one embodiment of the invention the monoclonal antibody which specifically forms a complex with amino acids 1-87 of PTHLP, which does not specifically form a complex with amino acids 1-34 of PTHLP and which forms a complex with the epitope to which any of the monoclonal antibodies produced by the hybridomas 212-10.7, (ATCC Accession No. HB9930) 199-999 (ATCC Accession No. HB9929) and 199-278 (ATCC Accession No. HB9931) is directed is labeled with a detectable marker. Examples of suitable detectable markers include an enzyme, biotin, a fluorophore, a chromophore, a heavy metal, a paramagnetic isotope, or a radioisotope. Additionally, in certain embodiments of the invention the monoclonal antibody is bound to a solid support such as a polymeric bead or glass or plastic surface.

In presently preferred embodiments, the invention also provides (1) a monoclonal antibody which is directed to the epitope to which the monoclonal antibody produced by the hybridoma 199-999 (ATCC No. HB9929) is directed; (2) a monoclonal antibody which is directed to the epitope to which the monoclonal antibody produced by the hydbridoma 199-278 (ATCC No. HB9931) is directed; and (3) a monoclonal antibody which is directed to the epitope to which the monoclonal antibody produced by the hybridoma 212-10. (ATCC No. HB9930) is directed.

Additionally, in one embodiment the invention provides the monoclonal antibody produced by, and the hybridomas 212-10.7 (ATCC No. HB9930); 199-278 (ATCC No. HB9931) and 199-999 (ATCC No. HB9929).

The present invention also concerns a method of detecting PTHLP in a biological fluid which comprises contacting the biological fluid with a monoclonal antibody which specifically forms a complex with amino acids 1-87 of PTHLP, which does not specifically form a complex with amino acids 1-34 of PTHLP, and which forms a complex with the epitope to which any one or all of the monoclonal antibodies produced by the hybridomas 99-999 (ATCC No. HB9929), 212-10.7 (ATCC No. HB9930), and 199-278 (ATCC No. HB9931) is directed under conditions such that the monoclonal antibody forms a complex with PTHLP, if present in the biological fluid; detecting any complex formed; and thereby detecting PTHLP in the fluid.

Conditions under which a monoclonal antibody of this invention forms a complex with PTHLP are well known in the art and may be readily determined by one skilled therein.

In one embodiment of the invention provides for the method of detecting PTHLP in a biological fluid, the monoclonal antibody is bound to a solid support. In another embodiment, the detecting comprises contacting any complex formed with a second antibody labeled with a detectable marker under conditions such that the second antibody binds to the complex and detecting labeled second antibody bound to the complex. Examples of detectable markers include an enzyme, biotin, a fluorophore, a chromophore, a heavy metal, a paramagnetic isotope, or a radioisotope.

Although the subject invention may be applied to any of the numerous commonly used biological fluids, in one embodiment of the above-mentioned method of detecting PTHLP, the biological fluid is selected from the group consisting of tissue extracts, urine, blood, and phlegm.

The invention also provides a method of determining the concentration of PTHLP in a biological fluid which comprises (a) contacting a solid support with an excess of a monoclonal antibody which specifically forms a complex with amino acids 1-87 of PTHLP, which does not specifically form a complex with amino acids 1-34 of PTHLP, and which forms a complex with the epitope to which any one or all of monoclonal antibodies produced by the hybridomas 212-10.7, (ATCC Accession No. HB9930) 199-999 (ATCC Accession No. HB9929) and 199- 278 (ATCC Accession No. HB9931) is directed, under conditions permitting the monoclonal antibody to attach to the surface of the solid support; (b) contacting the resulting solid support to which the monoclonal antibody is bound with a biological fluid sample under conditions such that the PTHLP in the biological fluid binds to the antibody and forms a complex therewith; (c) contacting the complex formed in step (b) with a predetermined amount of a second antibody labeled with a detectable marker and directed to an epitope on PTHLP, different from the epitope to which the monoclonal antibody of step (a) is directed, as to form a complex which includes PTHLP, the monoclonal antibody, and the second detectable antibody; (d) determining the amount of labeled antibody present in the complex formed in step (c); and (e) thereby determining the concentration of PTHLP in the biological fluid samples.

In one embodiment, the detectable marker with which the second antibody is labeled is an enzyme, biotin, a fluorophore, a chromophore, a heavy metal, a paramagnetic isotope, or a radioisotope.

In accordance with the teachings of the invention the second antibody may be a monoclonal antibody or a polyclonal antibody.

This invention also concerns a method of diagnosing humoral hypercalcemia of malignancy in a subject such as a human being which comprises obtaining from the subject a sample of a biological fluid, detecting PTHLP in the biological fluid using the above-described method, and thereby diagnosing humoral hypercalcemia of malignancy.

Examples of presently preferred biological fluids include tissue extracts, urine, blood, and phlegm.

This invention additionally provides a method of treating a subject such as a human being afflicted with humoral hypercalcemia of malignancy which comprises administering, for example, by intravenous administration to the subject an amount of a monoclonal antibody which specifically forms a complex with amino acids 1-87 of PTHLP, which does not specifically form a complex with amino acids 1-34 of PTHLP, and which forms a complex with the epitope to which any one or all of the monoclonal antibodies produced by the hybridomas 212-10.7, (ATCC Accession No. HB9930) 199-999 (ATCC Accession No. HB9929) and 199- 278 (ATCC Accession No. HB9931) is directed, effective to reduce the level or concentration of circulating PTHLP in the patient's biological fluid.

The present invention further provides a pharamaceutical composition which comprises an amount of a monoclonal antibody which specifically forms a complex with amino acids 1-87 of PTHLP, which does not specifically form a complex with amino acids 1-34 of PTHLP and which forms a complex with the epitope to which any or all of the monoclonal antibodies produced by the hybridomas 199-999 (ATCC No. HB9929), 212-10.7 (ATCC No. HB9930), and 199-278 (ATCC No. HB9931) is directed, effective to reduce the level of circulating PTHLP in the biological fluids of a human being afflicted with humoral hypercalcemia of malignancy and a pharmaceutically acceptable carrier.

Those skilled in the art will readily appreciate that amounts effective to reduce the level or concentration of circulating PTHLP in a human being's biological fluids may be readily determined and that any of the conventional pharmaceutically acceptable carriers useful for administering a monoclonal antibody may be employed such as sterile saline or buffers, liposomal formulations, and the like.

This present invention still further provides a method of detecting PTHLP in formalin-fixed, paraffin-embedded tissue sections which comprises contacting the tissue sections with a monoclonal antibody which specifically forms a complex with amino acids 1-87 of PTHLP, which does not specifically form a complex with amino acids 1-34 of PTHLP, and which forms a complex with the epitope to which any one or all of the monoclonal antibodies produced by the hybridomas 199-999 (ATCC No. HB9929), 212-10.7 (ATCC No. HB9930), and 199-278 (ATCC No. HB9931) is directed, under conditions such that the antibody binds to the tissue sections, detecting the antibody bound to the tissue sections, and thereby detecting PTHLP in the tissue sections.

Presently preferred for use in the preceding methods are tissue sections which are sections of a tissue in which normal tissue is characterized by the absence of PTHLP and neoplastic tissue is characterized by the presence of PTHLP in such tissue. Alternatively, the sections may be of a tissue in which normal tissue is characterized by the presence by PTHLP and neoplastic tissue is characterized by the presence of an elevated concentration of PTHLP in such tissue. Presently preferred are formalin-fixed, paraffin-embedded tissue sections, wherein the tissue comprises epithelial cells.

In one embodiment of the preceding method of detecting PTHLP in formalin-fixed, paraffin-embedded tissue sections, the monoclonal antibody is labeled with a detectable marker, such as an enzyme, biotin, a fluorophore, a chromophore, a heavy metal, a paramagnetic isotope or a radioisotope.

Optionally, the monoclonal antibody bound to the tissue sections may be detected by contacting the monoclonal antibody with a second antibody which is labeled with a detectable marker under conditions such that the second antibody binds to the monoclonal antibody and then detecting the second antibody so bound.

Suitable detectable markers comprises an enzyme, biotin, a fluorophore, a chromophore, a heavy metal, a paramagnetic isotope or a radioisotope.

Additionally, the invention provides a method of inhibiting the biological activity of PTHLP which comprises contacting PTHLP with an amount of a monoclonal antibody which specifically forms a complex with amino acids 1-87 of PTHLP, which does not specifically form a complex with amino acids 1-34 of PTHLP, and which forms a complex with the epitope to which any one or all of the monoclonal antibodies produced by the hybridomas 199-999 (ATCC No. HB9929), 212-10.7 (ATCC No. HB9930), and 199-278 (ATCC No. HB9931) is directed, effective to inhibit the activity of PTHLP.

The invention further provides a composition which comprises one of the above-described monoclonal antibodies to which an imaging agent is attached. Methods for attaching an imaging agent to a monoclonal antibody are, of course, well known to those skilled in the art.

Examples of suitable imaging agents include a paramagnetic isotope, a heavy metal, or a radioisotope.

The invention further provides a method of imaging humoral hypercalcemia of malignancy-associated tumor cells which comprises contacting the tumor cells with the above mentioned composition under conditions such that the composition preferentially binds to the tumor cells and detecting the composition so bound to the tumor cells.

The invention still further provides a therapeutic composition which comprises a monoclonal antibody which specifically forms a complex with amino acids 1-87 of PTHLP, which does not specifically form a complex with amino acids 1-34 of PTHLP, and which forms a complex with the epitope to which any of the monoclonal antibodies produced by the hybridomas 212-10.7, (ATCC Accession No. HB9930), 199-999 (ATCC Accession No. HB9931) and 199-278 (ATCC Accession No. HB9931) is directed, and to which a therapeutic agent is attached.

Examples of suitable therapeutic agents include toxins such as ricin, diptheria toxin, pseudomonas exotoxin-A, abrin, polkweed antiviral protein, saporin, and gelonin, as well as conventional therapeutic drugs.

Finally this invention provides a therapeutic method which comprises administering to a subject an effective amount of the above-described therapeutic composition.

EXPERIMENTAL DETAILS

Bacterial Strains and Plasmids

DH5α competent cells (F−, endAl, hsdR17 (r−$_k$,M+$_k$), sup44, thi-1, λ−, recAl, gyrA96, relAl, Δ(argF−, laczya) U169, φ80dlacZΔM15) were obtained from Bethesda Research Laboratories (Gaithersburg, Md.) and grown in LB broth media with 50 µg/ml ampicillin. Synthetic rPTHLP(1-141), rPTHLP(1-87) and trpE::PTHLP(19-87) were expressed in E. coli strain RR-1 (F−, hsdS20 (r−$_B$, m+$_B$), ara14, proA2, LacY1, galK2, rspL20, (Sm'), xyl-5, mtl-1, SupE 44, λ−). Vectors pATH-1 and pATH-3 were originated in Dr. Tzagoloff's laboratory (30) and plamid pTZ19R (2.9kb) was obtained from Pharmacia (Piscataway, N.J.). Cultures were grown in M9 media with 50 µg/ml ampicillin and 20 µg/ml tryptophan.

Oligonucleotide Synthesis

Oligonucleotides were synthesized using an Applied Biosystem Model 380 DNA Synthesizer using β-cyanoethyl phophoramidites as specified by the supplier and purified by denaturing 12% polyacrylamide gel electrophoresis and chromatography on Sephadex G25.

Gene Assembly and Cloning

Figure 1B:
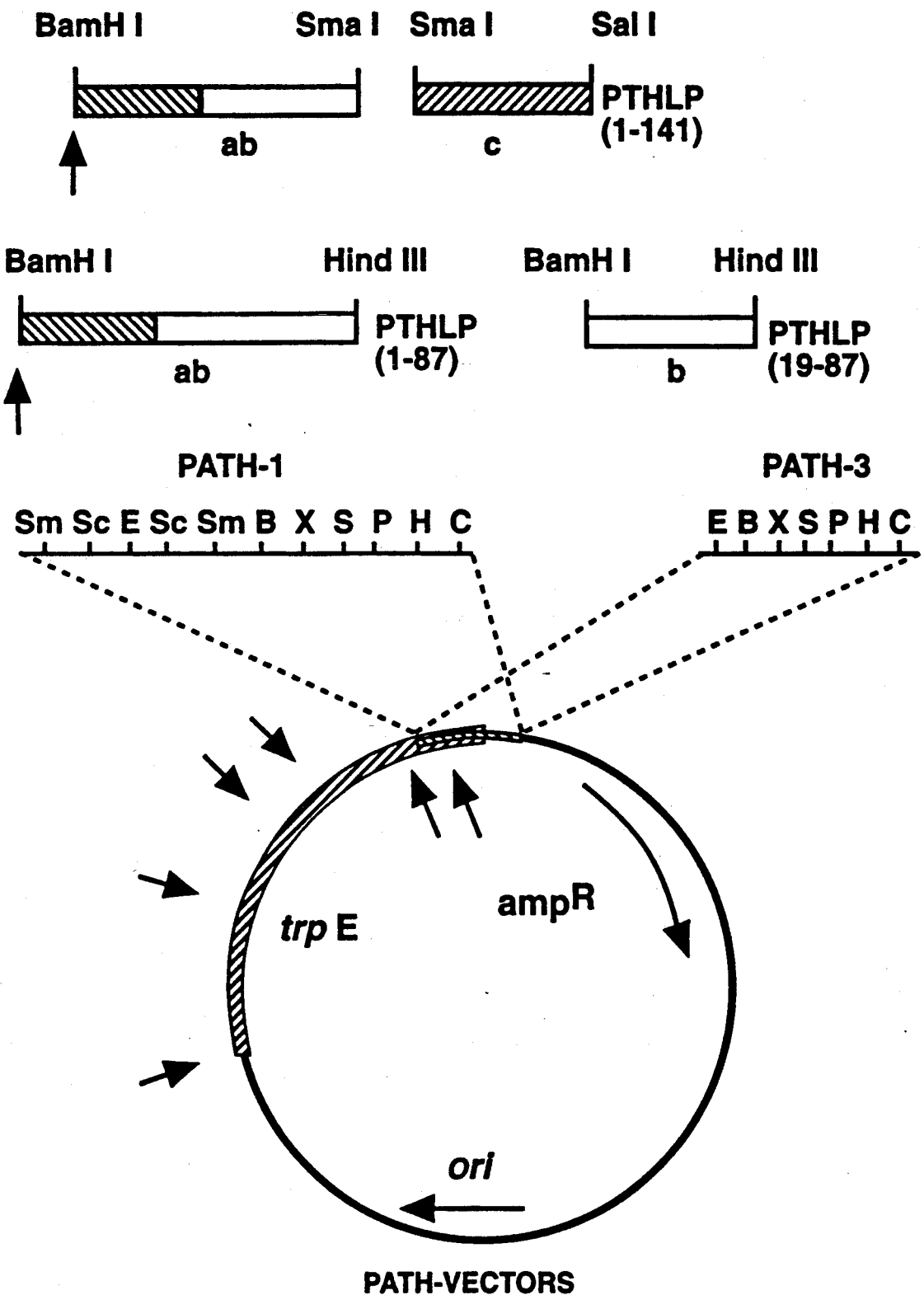
FIG. 1: Structure and expression of synthetic PTHLP genes.

Oligonucleotides 3-8 (segment b, FIG. 1) were phosphorylated (31), annealed and ligated into BamHI-HindIII sites of plasmid pTZ19R. The ligation mixture was used to transform competent DH5α cells. While ampicillin resistant colonies were selected at 37.C on LB-IPT6 x gal plates containing 50 µg/ml ampicillin. The resulting plasmid was called pTZ19R(b). Oligonucleotides 1 and 2 (segment a) were phosphorylated, annealed and ligated into BamHI-SalI sites.

Oligonucleotides 9-12 (segment c) were phosphorylated, annealed and ligated into BamHI-SalI sites pTZ19R, as described above, resulting in plasmid pTZ19R(c).

DNA from plasmid pTZ19R(ab) and pTZ19R(c) was examined by restriction analysis and subsequently sequenced (32) to confirm that segments ab and c contained the correct sequence.

The different PTHLP proteins were produced using expression vectors containing the whole gene or segments of the gene. Plasmid pTZ19R(ab) was digested with BamHI and SmaI and plasmid pTZ19R(c) was digested with SmaI and SalI, restriction fragments containing segments ab and c were purified from agarose gels and ligated to vector pATH-1. The resulting plasmid pATH-PTHLP(1-141) was used for bacterial production of rPTHLP(1-141).

The same expression vector was used to produce rPTHLP(1-87). Segment ab was obtained from plasmid pTZ19R(ab) after digestion with BamHI and HindIII and cloned into the same restriction sites in pATH-1. Finally, expression vector pATH-3 was used in the construction of the pATH-PTHLP(19-87) plasmid which was used in the production of this trpE::PTHLP fusion protein. Plasmid pTZ19R(b) was digested with BamHI and HindIII and the restriction fragment containing segment b was cloned into BamHI-HindIII sites in pATH-3.

Transformation of pATH expression vectors was accomplished using competent RR-1 cells, and ampicillin resistant clones were selected on LB plates containing 50 μg/ml ampicillin and 40 ug/ml tryptophan.

Bacterial Expression of PTHLP Proteins

Bacteria (*E. coli* strain RR-1) containing the expression plasmids were grown in M9 media with 20 μg/ml tryptophan and 50 μg/ml ampicillin for 12 hrs. at 37° C. Cells were washed in M9 media and diluted 1:100 in M9 media with 50 μg/ml ampicillin with no tryptophan and incubated at 20° C. for 2 hrs. Expression of the fusion proteins was induced by adding 5 μg/ml indoleacrylic acid and the cells were incubated under the same conditions for 4 hrs. The cells were chilled on ice, harvested by centrifugation, washed once with sonication buffer (20 mM Tris-HCL, pH 8.0, 2 mM EDTA, 100 mM Nacl, 10 mM 2-mercaptoethanol) and stored at −70° C. until they were used for protein purification.

Purification of Recombinant Fusion Proteins a. rPTHLP(1-141)

Induced bacterial pellets were thawed in ice water and disrupted by sonication in 20 mM sodium phosphate, pH 6.5, containing 10 mM 2-mercaptoethanol, 7M guanidine hydrochloride and 1 mM phenylmethylsulfonylfluoride. Sonicates were clarified by centrifugation (Dupont Sorval, SS34 rotor) for 15 min at 15,000 RPM and applied to a Sephacryl S-200 gel filtration column (5 cm diameter×100 cm) equilibrated with the same buffer containing 4 M guanidine hydrochloride. Fractions containing the trpE::PTHLP fusion protein were identified by sodium dodecyl sulfate-polyacrylamide gel electrophoresis (SDS-PAGE) analysis and immunoblotting with a rabbit antisera produced against a synthetic peptide (PRP-1) corresponding to amino acids 34-53 of PTHLP(1-141) (see below). Pooled material was dialyzed against 1% (v/v) formic acid, adjusted to 70% formic acid, and the trpE::PTHLP(1-141) fusion protein was cleaved using a 2000-fold molar excess of CNBr for 24 hr. Following extensive dialysis against 0.1M acetic acid, the mixture was passed over a polyethyleneimine anion exchange column (1 cm×10 cm, WP-PEI, J. T. Baker Chemical Company, Phillipsburg, N.J.). The flow through material from this column contained the rPTHLP and was applied directly to a carboxyethyl cation exchange column (1 cm×20 cm, WP-CBX, J. T. Baker). Elution of rPTHLP(1-141) was achieved using a linear gradient from 80% 10mM sodium phosphate, pH 7.0 20% 1M sodium phosphate,to 55% 10 mM buffer/45% 1M buffer over a period of 2 hr at a flow of 1 ml per min. The fractions containing rPTHLP eluted at or above 35% 1M sodium phosphate and were dialysed against 0.01M acetic acid, made 0.05% with trifluoroacetic acid (TFA) and applied to a semipreparative C-18 reverse phase HPLC column (Waters, Milford, Mass.). The rPTHLP was eluted using a gradient of 0 to 30% acetonitrile (30 min) followed by a gradient of 30 to 34% acetonitrile (2 hr); 0.05% TFA was the counterion at a flow of 1 ml per min.

b. rPTHLP(1-87)

Induced bacterial pellets were thawed in ice water and disrupted by sonication in 70% formic acid. Particulate material was removed by centrifugation at 15,000 rpm in an SS34 rotor. 1 gram of CNBr was added per gram of original cell pellet and cleavage was allowed to proceed for 24 hr at room temperature. Following extensive dialysis against 0.1M acetic acid, TFA was added to 0.1 and the solution was applied to a semipreparative reverse phase (C18) HPLC column (Waters, Milford, Mass.). Chromatography proceeded using 0.1% TFA as counterion and elution of rPTHLP(1-87) achieved using a linear gradient of increasing acetonitrile from 0 to 60% over the period of 1 hr. Fractions containing rPTHLP(1-87) were identified by immunoblotting with polyclonal rabbit antisera recognizing residues 34-53 of PTHLP. These fractions were pooled, diluted 5-fold with 0.1% TFA and reapplied to the reverse phase HPLC column. With 0.1% TFA as counterion, a second linear gradient of increasing acetonitrile from 0 to 20% at 15 min and then to 60% after 2 hr was carried out and the fractions containing rPTHLP(1-87) were again identified by immunoblotting. The purity of each fraction was assessed by coomassie staining of 15% SDS-polyacrylamide gels and the fractions were stored separately at −70° C.

c. trpE::PTHLP(19-87)

Induced bacterial pellets were thawed in ice-water and disrupted by sonication in 20 mM sodium phosphate, pH 6.5, containing 10 mM 2-mercaptoethanol, 7M guanidine hydrochloride and 1mM phenylmethylsulfonylfluoride(PMSF). Sonicates were clarified by centrifugation (Dupont Sorval, SS34 rotor) for 15 min at 15,000 RPM, filtered through a 0.22 μm filter, diluted 5-fold with 0.02M Tris-HCL (pH 8.5) and applied to a DEAE TSK FPLC column (anion exchange) (1.5 cm×25 cm). The fusion protein was eluted using a linear gradient from 0.02M Tris-HCl (pH 8.5) to 0.02M Tris-HCl (pH 7.0) containing 0.3M NaCl over a period of 30 min with a flow rate of 2 ml/min. Fractions containing the 53,000 molecular weight fusion protein were determined by 12% SDS polyacrylamide gel electrophoresis, pooled, lyophilized and applied to a fractogel TSK 55S column (1.5 cm×100 cm) in PBS. The elution profile was developed with a flow rate of 0.75 ml/min and the fractions were analyzed by 12% SDS polyacrylamide gel electrophoresis. Fractions containing trpE::PTHLP(19-87) were pooled and stored at −70° C.

SDS-PAGE Electroelution

Following SDS-polyacrylamide gel electrophoresis rPTHLP(1-141) was identified by staining 1 min with coomassie brilliant blue and the protein band sliced from the gel. The gel slice was placed in a pasteur pipette, ground with a glass rod, and suspended in electroelution buffer (50 mM ammonium bicarbonate, 1 mM sodium EDTA, and 0.2% SDS). A paper wick was used to connect the pasteur pipette to the upper reservoir and the rPTHLP(1-141) was electroeluted by anodal migration (5 hrs at 100 volts) into dialysis tubing submerged in the lower reservoir. Once eluted, the polypeptide was dialyzed against 50mM sodium phosphate, pH 7.0, containing 5 mM 2-mercaptoethanol and 0.2% SDS. Following dialysis a solution of 100% trichloroacetic acid was added to a final concentration of 30% and the mixture allowed to sit on ice for 3 hr. The protein was precipitated by centrifugation at 3000 rpm in a Beckman TJ-6 centrifuge, washed with ice cold acetone saturated with sodium chloride, and dissolved in deionized water.

Adenylate Cyclase Assays

PTHLP bioactivity was assayed by measuring the conversion of $[\alpha^{32}P]$-ATP (Amersham) to 32P-cAMP catalyzed by adenylate cyclase in a canine renal membrane preparation. The membranes were prepared and the assay performed as described previously (7,33). Characterization of adenylate cyclase activity present in each membrane preparation was accomplished using the standard synthetic peptides bovine PTH (1-84) (Bachem, Torrance, Calif.) and amino acids 1-37 of PTHLP (termed PTH-related protein by Peninsula Laboratories). Activity is reported as the percent of basal adenylate cyclase activity (ie. activity in the presence of vehicle only). The specificity of the assay for PTH receptor was shown by use of the PTH antagonist $[Nle^{8,18}, Tyr^{34}]$-bovine PTH(3-34) amide (Bachem) which competes with PTH for binding to the receptor but does not activate adenylate cyclase (34).

The rat osteosarcoma cell line 17/2.8 was also used to determine adenylate cyclase-stimulating activity. This assay was performed as described previously (10,13). The peptides were added to duplicate wells containing confluent ROS 17/2.8 cells which had been prelabeled with $[^3H]$-adenine, and were incubated at 37° C. for 10 min in 5% $CO_2$. Adenylate cyclase activity (production of $[^3H]$-cAMP) is expressed as described for the renal assay.

Bone Resorption Assay

Measurement of $^{45}Ca$ release from fetal rat long bones was perfomed as described previously in detail (35). Briefly, 18-day pregnant Sprague-Dawley rats were injected with $^{45}Ca$ and fetal rats removed the following day. Fetal radii and ulnae were incubated for 72 hours with either control or rPTHLP(1-141) containing medium. Results are expressed as the ratio of treated compared to control bones (35).

In vivo Infusion Studies

Infusion of rats with rPTHLP(1-141) was accomplished using osmotic minipumps (model 2001: Alza Corp., Palo Alto, CA) as described previously (25). Recombinant PTHLP(1-141) was infused in a vehicle consisting of 150 mM NaCl, 1 mM HCl, and 2% cysteine-HCl. Serum calcium levels were determined daily from tail vein bleeds using atomic absorption spectrophotometry. In order to ascertain the stability of rPTHLP(1-141) during the five day infusion, the remainder of the infused peptide was removed at the end of the infusion and assayed for bioactivity; after five days in the Alzet pumps, rPTHLP(1-141) retained full bioactivity in the renal adenylate cyclase assay.

Production of Polyclonal Antisera

The development of a two-site immunometric assay involved the use of a monoclonal antibody for capture of the antigen and a polyclonal reporter. The recombinant fusion proteins trpE::PTHLP(19-87) or the synthetic peptides PTHLP(1-37) or PTHLP(34-53) were used to prepare rabbit polyclonal sera against PTHLP. Peptide PRP-1 containing amino acids 34 to 53 of the published sequence of PTHLP (18,19) was synthesized in an Applied Biosystems peptide synthesizer model 430A using tBoc chemistry. The peptide was coupled to keyhole lympet hemocyanin via glutaraldehyde and used for the immunization of rabbits.

A rapid immunization protocol was followed which previously produced antisera with high titers against a variety of protein antigens. Following an initial perilymph nodal immunization (500 μg antigen animal in Freund's complete adjuvant) subsequent biweekly, intramuscular boosts (250 μg antigen animal in Freund's incomplete adjuvant) were suceeded after 10 days by serum collection. The sera was tested by immunoblotting of rPTHLP polypeptides.

Immunoglobulin specifically reactive with the PTHLP was purified from hyperimmune rabbit sera by affinity chromatography. Affinity chromatography columns were prepared using commercially available Affiprep 10 (BioRad) which was coupled to the appropriate antigen at a ratio of 2–10 mg/ml packed resin. Antisera were centrifuged at 10,000×g for 30 min. to remove any particulate material and applied to the affinity column by cycling the antisera over the column at a flow rate of 0.5 ml/min. The column was then washed extensively with PBS followed by PBS containing 1M NaCl at 2 ml/min. The specifically bound immunoglobulin was then eluted from the column with 50 mM glycine-HCl, pH 2.0 at 2 ml/min. Fractions of 2 ml were collected into tubes containing 0.1 ml of 2M Tris-HCl, pH 8.0.

Production of Monoclonal Antibodies

Production of monoclonal antibodies followed standard procedures which have been utilized extensively in our laboratories. Following the immunization schedules given in Table 2 mice with the strongest immune response were sacrificed by cervical dislocation, their spleens removed, and their splenic lymphocytes isolated in RPMI 1640 media (M.A. Bioproducts, Walkerville, Md.). Erythrocytes were lysed by treatment with 0.17M ammonium chloride and the spleen cells counted in a hemocytometer. Fusions were conducted using a ratio of seven spleen cells to one myeloma cell, Ag 8.653 which does not express heavy or light chains of immunoglobulin before hybridoma formation (36). Cells were centrifuged at 200×g for 5 min and resuspended in 35% polyethylene glycol (1300–1600 molecular weight, ATCC, Rockville, Md.), and centrifuged at 200×g for 6 min. The fused cell pellet was suspended in 5 RPMI 1640 supplemented with 20% fetal calf sera (Hyclone Laboratories), 1.0 mM sodium pyruvate and 10% NCTC 109 medium (MA Bioproducts) and cultured in a T150 flask at 37° C., in a humidified 7% $CO_2$ - 93% air incubator overnight. The following day the media was 10 supplemented with $1 \times 10^{-4}$M hypoxanthine, $4 \times 10^{-7}$M aminopterin, and $1.6 \times 10^{-5}$M thymidine and plated in microtiter plates (Costar, Cambridge, Mass.) at $10^6$ cells per well.

After 10 to 12 days of incubation at 37° C., culture fluids from wells containing actively growing hybrid colonies were harvested and an ELISA assay using rPTHLP(1-141) used for primary screening. Positive subclones were expanded, subcultured and where appropriate rescreened by antigen capture assay, immunoprecipitation and immunoblotting (see below).

To obtain standard preparations of monoclonal antibody, hybridoma cells ($3.0 \times 10^7$) were cultured for 2 h in serum-free culture medium and injected into the peritoneal cavity of pristane-pretreated BALB/c mice. Ascites fluid was harvested within 7 to 10 days and clarified by centrifugation at 2,500×g for 10 min. IgG was purified by ammonium sulfate precipitation and ion exchange chromatography using Waters HPLC instrumentation. Production of IgG from hybridoma tumor ascites typically yields several hundred milligrams of the desired antibody from a small number of mice. Another approach to immunoglobulin isolation, useful for small scale batches, was to grow hybridoma cells in defined, serum-free medium (e.g. HB101, HANA Biologicals) and to purify IgG directly from culture supernatants. This method was found to be well suited to isolating immunoglobulin in quantities of about 5 to 25 mg.

Screening of Hybridoma Supernantants Primary Screen—ELISA Assay 96 well polystyrene microtiter assay plates were coated overnight at 4° C. or 3 hr. at 37° C. with 50 μl/well of 0.1M $NaHCO_3$, pH 9.0 containing 25 ng of antigen. The wells were rinsed twice with PBS-0.05% Tween 20 (PBST) and then blocked for 1 hour with 150 μl of PBS-1%BSA. After rinsing twice with PBST 50 μl of hybridoma supernatant was added and the plates were incubated for 1 hour at room temperature. Following 4 rinses with PBST 50 μl of PBS-0.1% BSA containing 1/1000 rabbit anti-mouse IgG conjugated to alkaline phosphatase (Zymed, San Francisco, Calif.) was added to each well and the plate was incubated at room temperature for one hour. Four more rinses with PBST were followed by addition of 50 ul of substrate solution (p-nitrophenol phosphate, disodium, Sigma, St. Louis, Mo.), prepared by adding 1 pellet to 5 ml of diethanolamine buffer (9.7% diethanolamine, 0.02% $NaN_3$, 0.01% $MgCl_2$, pH 9.8). The was stopped by addition of 50 μl of 3M NaOH and the absorbance at 405 nm was determined.

Antigen Capture Assay 96 well polystyrene microtiter assay plates were coated overnight at 4° C. or 3 hr at 37° C. with 50 μl/well of 0.1M $NaHCO_3$, pH 9.0 containing 5 μg/ml goat anti-mouse IgG, affinity purified-heavy and light chain specific (Cappel, Malvern, Pa.). After rinsing 2 times with PBST the wells were blocked by incubation for 1 hour at room temperature with 150 μl/well of PBS-1% BSA and then again rinsed twice with PBST. 50 μl/well of hybridoma supernatant was added and another incubation, 2 hour at room temperature, was followed by 4 rinses with PBST. Incubation with antigen, trpE::PTHLP(1-141) or trpE::PTHLP(19-87), in 50 μl/well of PBS-0.1% BSA for 2 hour at room temperature was followed by 4 rinses with PBST and an incubation, 2 hour at room temperature, with 50 μl/well of the trpE gene product region specific monoclonal antibody, F123-278. After 4 more rinses with PBST, 1/1000 rabbit anti-mouse IgG conjugated to alkaline phosphatase, 50 μl/well in PBS-0.1% BSA, was added and a final incubation of 1 hour at room temperature was carried out. After 4 rinses with PBST, 50 μl/well of substrate solution (see above) was added, the reaction stopped after 15 min. with 3M NaOH and the absorbance at 405 nm was determined.

Immunoprecipitation

Immunoprecipitation of either rPTHLP(1-141) or rPTHLP(1-7) was accomplished with the polypeptides labeled using iodobeads (Pierce). Iodination was carried out at room temperature for 4 min. with 50 μg of polypeptide in 250 μl of PBS to which 1 mCi of Na $^{125}$I and 1 iodobead were added. The reaction was stopped and free $^{125}$I removed by gel filtration using a PD10 column (Pharmacia, Piscataway, N.J.) pre-blocked with PBS-0.1% BSA.

The procedure for immunoprecipitation was as follows. 50 μl of hybridoma supernatant was mixed with 50,000 cpm of $^{125}$I-labeled antigen, brought to a total volume of 150 μl with PBS-1% BSA and incubated overnight at 4° C. in a conical polystyrene test tube (Sarstedt, W. Germany). 50 μl of protein A-agarose (BRL, Gaithersburg, Md.) in PBS-0.02% NaN was then added and the mixture was incubated for 2 hours at room temperature with vigorous shaking. Subsequently, the immunoprecipitate was collected by centrifugation for 5 min. at 3000 rpm in a Beckmann TJ-6 table top centrifuge and the supernatant removed. After washing one time with 3 ml of PBS the bound antigen was determined using an LKB gamma counter, model 1277 Gammamaster.

Immunoblotting 50 ng/lane of rPTHLP(1-141), rPTHLP(1-87) or 10 μl/lane of the uninduced E. coli vector lysate was applied to a 15% SDS-polyacrylamide gel and electrophoresis carried out at 35 volts, overnight at room temperature. The protein was then transferred to nitrocellulose paper (BioRad, Hercules, Calif.) using a Sartorius semi-dry electroblotter. The transfer was carried out at 200 mAmps for 2 hours using electrophoresis running buffer containing 15% methanol and 0.1% SDS as the buffer. Following transfer the nitrocellulose was blocked with TBS-0.05% Tween-20 (TBST) containing 0.5% powdered milk. the nitrocellulose was then sliced into strips (0.2 cm width) and each strip incubated 2 hours at room temperature with 200 μl hybridoma supernatant diluted with 600 μl TBST-0.5M NaCl before addition of 1 ml TBST-0.5M NaCl containing 1/7500 goat anti-mouse IgG conjugated to alkaline phosphatase (Promega, Madison, Wis.). After 1 hour at room temperature the nitrocellulose was washed 3 times for 5 min. with TBST-0.5M NaCl and once for 5 min. with 100 mM Tris, 100 mM NaCl, 5 mM MgCl$_2$, pH 9.5. Color development was then achieved in the same buffer with 33 μl/5 ml Nitro Blue tetrazolium and 66 μl/5 ml 5-bromo-4-chloro-3-indolyl-phosphate (Promega).

Isotyping of Immunoglobulin 96 well polystyrene microtiter assay plates were coated overnight at 4° C. or 3 hours at 37° C. with 50 μl/well of 0.1M NaHCO$_3$, pH 9.0, containing 50 ng of rPTHLP(1-141). After rinsing twice with PBST, 150 μl/well of PBS-1% BSA was added and blocking proceeded for 1 hour at room 1 temperature before rinsing twice with PBST. 50 μl/well of 8 isotyping reagents (Southern Biotechnology, Birmingham, Ala.) was added at a dilution of 1/500 in PBS-0.1% BSA and incubated 1 hour at room temperature. The were then washed 6 times with PBST and 50 μl/well of substrate solution added. After 15 min. the reaction was stopped with 50 μl/well of 3M NaOH and the absorbance at 405 nm determined.

Two-Site Immunometric Assay for PTHLP 96-well polystyrene microtiter plates were coated overnight at 4° C. with 50 μl of the first monoclonal antibody at 5 μg/ml in 0.1M sodium bicarbonate, pH 9.0. After washing the wells 4 times for four minutes each (4×4) with Phosphate buffered Saline - 0.05% Tween-20 (PBST), 150 μl of PBS - 1% BSA was added per will and blocking of nonspecific-protein binding sites was achieved by incubation for 1 hr at room temperature. The plates then washed 4×4 min with PBST before 50 μl of sample or standard (PTHLP(1-87)) in a medium comparable to that of the sample, e.g. normal human serum) was added per well and incubated overnight at 4° C. The plates were then washed 4×4 min with PBST and 50 μl of 5 μg/ml affinity-purified rabbit polyclonal antisera, OG 136, was added to each well. Following a 1 hr incubation at room temperature the plates were washed 4×4 min with PBST, 50 μl of Zymed goat anti-rabbit IgG conjugated to alkaline phosphatase was added at a 1000-fold dilution in PBS - 0.1% BSA and the plates were incubated 1 hr at room temperature. After washing 4×4 min with PBST, 50 μl of Sigma phosphate substrate (p-nitrophenolphosphate) in 9.7% diethanolamine, 0.01% MgCl$_2$ 6H$_2$O, 0.02 NaN$_3$ was added to each well and, following a 45 minute incubation at room temperature, the absorbance at 405 nm was determined using a Bio Tek Microplate reader, model 320.

Neutralization of PTHLP Bioactivity

The ability of PTHLP-specific monoclonal antibodies to inhibit the bioactivity of PTHLP was determined using the canine renal membrane adenylate cyclase assay after preincubating purified rPHTLP or a biological sample in the presence or absence of the monoclonal antibody for 1 hr at room temperature. The incubation volume was adjusted to 30 μl with buffer containing 0.25M sucrose, 1.0 mM EDTA and 5.0 mM Tris-HCl, ph 7.5. Siliconized eppendorf centrifuge tubes were used. After the incubation each sample was divided into 3 equal aliquots and the remaining bioactivity was determined using the canine renal membrane adenylate cyclase assay (see above).

RESULTS

Chemical Synthesis of PTHLP Genes

Based on the nucleotide sequence of the PTHLP gene, 12 Overlapping oligonucleotides were designed to construct the complete synthetic gene, encoding 141 amino acids, as well as shorter versions of this gene (encoding amino acids 1-87 and amino acids 19-87). Bacterial codons and convenient restriction sites were chosen to facilitate manipulation of synthetic gene fragments.

Bacterial PTHLP proteins were produced as fusion proteins with the trpE gene product since such a construct could potentially increase stability of the synthetic product. The vector was designed such that rPTHLP(1-87) and rPTHLP(1-141) were separated by a methionine residue from the rest of the fusion protein. Thus, intact rPTHLP species could then be released by CNBr cleavage since there are no methionine residues in the PTHLP polypeptides.

Oligonucleotides were synthesized and grouped to generate three segments (FIG. 1) a, b and c. These segments were ligated, as indicated in Methods, to generate plasmids pTZ19R(b), pTZ19R(ab) and pTZ19R(c). The synthetic inserts in these plasmids were verified by restriction analysis and sequencing. Segment ab alone, or after ligation to segment c, was cloned into the pATH-1 vector to generate the pATH-PTHLP(1-87) and pATH-PTHLP(1-141) plasmids which contain a fused gene coding for a total of 439 and 493 amino acids, respectively. The construct consisted of 338 amino acids from the bacterial protein anthranilate synthase, 14 amino acids from the synthetic polylinker and 87 or 141 amino acids from pTHLP.

Segment b encoding amino acids 19-87 was cloned in vector pATH-3 to generate plasmid pATH-PTHLP(19-87) which produced a fused gene encoding a total of 413 amino acids, 338 from anthranilate sythase, 7 from the synthetic polylinker and 68 from PTHLP.

Plasmids pATH-PTHLP(1-87) and pATH-PTHLP(1-141) were used for bacterial production of rPTHLP(1-87) and rPTHLP(1-141). Plasmid pATH-PTHLP(19-87) was used for bacterial production of the trpE::PTHLP(19-87) fusion protein.

Bacterial Expression and Purification of rPTHLP species

Lysates of bacterial cultures harvested after tryptophan starvation and trpE induction were analyzed by SDS-PAGE. When sufficient induction of a protein species with the appropriate apparent molecular weight (53,000 for trpE::PTHLP(1-141); 42,000 for trpE::PTHLP(19-87); 45,000 for trpE::PTHLP(1-87)) was observed, and confirmed by immunoblotting with an affinity purified antisera recognizing the synthetic peptide PTHLP(34-53), purification of the recombinant proteins was carried out according to the procedures described under Methods. rPTHLP(1-141)was purified to homogeneity and amino-terminal sequence analysis revealed the expected amino acid sequence for positions 1-28. rPTHLP(1-87) had minor contaminants with apparent molecular weights lower than than that of rPTHLP(1-87). However, these were shown to be fragments of PTHLP(1-87) itself, rather than bacterial contaminants, by immunoblotting with the PTHLP(34-53)-specific antisera. trpE::PTHLP(19-87) was purified to approximately 90-95% homogeneity, although some bacterial contaminants remained.

Biological Activity of rPTHLP Polypeptides

The biological activities of rPTHLP(1-87) rPTHLP(1-141) and rPTHLP(1-87) were determined using the canine renal membrane adenylate cyclase assay. The results of such an assay are shown in Table 1 along with the activities obtained using the synthetic peptides bPTH(1-34) and [Tyr$^{36}$]-PTHLP(1-36) amide as standards. All of the PTHLP peptides were active in this assay although at significantly higher concentrations than bPTH(1-34). A more detailed investigation of the activity of homogenous rPTHLP(1-141) revealed that in an assay involving the stimulation of adenylate cyclase in rat osteosarcoma cells (ROS) the relative activities of bPTH(1-34) and rPTHLP(1-141) were reversed from those in the canine renal membrane system (Table 1). In the same study rPTHLP(1-141) was shown to stimulate the release of $^{45}$Ca from fetal rat long bones and to cause in vivo hypercalcemia, when infused into rats, with a potency similar to that of bPTH(1-34) (Table 1). The importance of the different relative activities in different bioassays is not yet clear since the physiologic role of PTHLP is still unknown.

Further evidence of the similarity of action between rPTHLP species and PTH is shown in FIG. 2. In this experiment the competitive antagonist of PTH binding to its cell surface receptor, [Nle$^{8,18}$, Tyr$^{34}$]-bPTH(3-34) amide, was used to inhibit the activities of hPTH(1-84), PTHLP(1-37), rPTHLP(1-141) and rPTHLP(1-87). The three parallel inhibition curves indicate that all of these polypeptides stimulate adenylate cyclase via the same receptor in canine renal membranes.

18 bleed the mice. At day 19 test the mice serum for the presence of PTHLP antibodies using 50 micrograms PTHLP (34-53) on polystyrene beads.

The mice rested for 3 months. At day 0' inject the mice intraperitoneally, with 50 micrograms trpE::PTHLP (19-87). At day 8' bleed the mouse. At day 28' inject the mice with 50 micrograms trpE::PTHLP (19-87). Bleed the mice again at day 38'. At day 45' inject the mice, intraperitonal, with 20 micrograms PTHLP (1-141). At day 47' reinject the mice, intraperitonal, with 20 micrograms PTHLP (1-141). Day 48' reinject the mice, intraperitonal, with 20 micrograms PTHLP (1-141). At day 49' fuse spleenocytes and myeloma cells.

The immunization schedule which produced fusion 199 are as follows. At day 0 mice with 100 micrograms trpE::PTHLP (19-87). At day 7 inject mice with 100 micrograms trpE::PTHLP (19-87). At day 14 inject mice with 100 micrograms trpE::PTHLP (19-87). At day 24 test bleed the mice. At day 28 inject mice with 100 micrograms trpE::PTHLP (19-87). At day 28 inject the mice with 100 micrograms trpE::PTHLP (19-87). At day 30 inject the mice with 100 micrograms trpE::PTHLP (19-87) and at day 31 fuse spleenocytes and myeloma cells.

The primary screen used for each fusion was an ELISA involving rPTHLP(1-141) coated onto 96 well microtiter assay plates. Hybridoma supernatants from colonies testing positive by the primary screen were then assayed by numerous secondary screens including:

1. Two-site immunometric assays involving goat anti-mouse IgG on 96-well microtiter assay plates for immobilization of secreted immunoglobulin, either trpE::PTHLP(1-141) or trpE::PTHLP(19-87) as

TABLE 1

Bioactivities of PTHLP Peptides

| Peptide | Adenylate Cyclase Canine Assay | Stimulation$^a$ ROS assay | $^{45}$Ca Release$^b$ | In Vivo Hypercalcemia |
|---|---|---|---|---|
| bPTH(1-34) | $1.5 \times 10^{-10}$M | $2 \times 10^{-9}$M | $1 \times 10^{-10}$M | 0.17 μg/hr (37) |
| [Tyr$^{36}$]-hPTHLP (1-36) amide | $1.5 \times 10^{-9}$M | $1.5 \times 10^{-9}$M(25) | $1 \times 10^{-9}$M(25) | 0.14 μg/hr (25) |
| PTHLP(1-141) | $1 \times 10^{-8}$M | $4 \times 10^{-10}$M | $1 \times 10^{-8}$M | 0.7 μg/hr |
| PTHLP(1-87) | $1 \times 10^{-8}$M | N.D. | N.D. | N.D. |

$^a$The values correspond to the hormone concentration required for 50% of maximum bioactivities of PTHLP peptides stimulation of adenylate cyclase activity.
$^b$The values correspond to the hormone concentration required for elevation of $^{45}$Ca release above control levels (P < 0.05).
$^c$The values correspond to the minimum infusion rate required to cause hypercalcemia within 3 days.
N.D. = Not Determined These activity data for rPTHLP species confirm that PTHLP has the characteristics expected of a putative factor responsible for HHM. In addition, they indicate that the recombinant polypeptides used for immunizations, screening of antibodies and also as standards for immunometric assays have both the correct primary sequence and the necessary secondary and tertiary conformations required to develop immunoreagents for sensitive detection of native PTHLP species.

Production of Monoclonal Antibodies

Three fusions, 199, 212 and 214 have thus far yielded hybridomas secreting monoclonal antibodies recognizing PTHLP. The immunization schedules of the mice used for these fusions were as follows.

To produce fusions 212 and 214 mice were immunized at day 0 with 20 micrograms PTHLP (34-53)-KLH, S.Q. At day 7 subcutaneously injected mice with 20 micrograms PTHLP (34-53)-KLH. Day 18. At day antigen and a trpE specific monoclonal antibody (F123-278) as the second antibody.
2. Immunoprecipitation of $^{125}$I-labeled rPTHLP(1-141) or rPTHLP(1-87).
3. Immunoblotting against rPTHLP(1-141), rPTHLP(1-87), or uninduced bacterial vector lysate.

Sixteen stable hybridomas secreting PTHLP-specific monoclonal antibodies were isolated from these three fusions. All of these antibodies recognized both rPTHLP(1-141) and rPTHLP(1-87). Their clone numbers, isotypes and epitope specificities are listed in Table 3.

Despite the ability of each MAb to recognize rPTHLP(1-87), only 7 out of the 16 MAbs recognized any of the 3 synthetic peptides, listed in Table 2, which cover the entire length of the 87 amino acid polypeptide. There are two possible explanations for this. First, it is possible that the monoclonal antibodies recognize epitopes containing primary sequences which overlap from peptide to peptide, or second, that the monoclonal antibodies recognize conformational epitopes not present in the smaller synthetic peptides.

Biologically Relevent PTHLP Species

As stated in the introduction, immunoassays capable of specific detection of PTHLP in biopsy samples or serum from cancer patients, and possibly patients with other clinical conditions, will allow differentiation of hypercalcemia due to PTHLP versus other causes such as primary hyperparathyroidism. However, many immunoassays including the presently available radioimmunoassay recognizing PTHLP(1-34) are not suitable for use with such samples. We have therefore developed imunoassays, using the unique immunological reagents described herein

TABLE 2

Monoclonal Antibody Characteristics

| Clone[a] | Epitopes[b] | | | | (1-87) | (1-141) | Immunoblot (1-87) | Immunoprecipitation (1-87) |
|---|---|---|---|---|---|---|---|---|
| | (1-34) | (34-68) | (67-86) | (19-87) | | | | |
| 212-1 | − | + | − | + | + | + | +++ | ++ |
| 212-2 | − | + | − | + | + | + | + | + |
| 212-3 | − | + | − | + | + | + | +++ | +++ |
| 212-5 | − | + | − | + | + | + | +/− | ++ |
| 212-6 | − | + | − | + | + | + | +++ | ++ |
| 212-7 | − | − | − | + | + | + | +++ | +++ |
| 212-8 | − | − | − | + | + | + | +++ | +++ |
| 212-10 | − | + | − | + | + | + | ++ | +++ |
| 212-11 | − | − | − | + | + | + | +++ | ++ |
| 212-13 | − | + | − | + | + | + | − | ++ |
| 212-14 | − | − | − | + | + | + | +++ | ++ |
| 212-16 | − | − | − | + | + | + | +++ | − |
| 214-17 | − | − | − | + | + | + | +++ | ++ |
| 214-18 | − | − | − | + | + | + | +++ | ++ |
| 199-278 | − | − | − | + | + | + | +++ | ++ |
| 199-999 | − | − | − | + | + | + | +++ | +++ |

[a]All isotypes determined were IgG2A, k except clones 212-2 and 212-3 whose isotypes are both IgG2A and IgG3.
[b]Determined by ELISA.

to overcome these problems.

A question which had to be answered for such assays are to have clinical significance involved the biologically relevant forms of the polypeptide (i.e. those species of PRTHLP found in normal and malignant tissues or present in the circulation). Studies have been complicated by the unusual physiochemical properties of PTHLP, most notably its extremely basic isoionic point (>11.0 as determined by chromatofocusing) which causes the protein to bind ionicaly to non-specific immunoglobulin, other proteins and also to chromatographic matrices such as those commonly used for gel filtration. Appropriate conditions, such as the inclusion of 6M urea in gels and chromatography buffers, allow analysis of tissue and tumor specific PTHLP species by comparison of the bio- and immuno-reactivity of these polypeptides.

To overcome the artefacts associated with complex bio-logical fluids, such as serum, a two-site immunometric assay has been developed as described under Methods. A diagram of the assay is shown in FIG. 3. The monoclonal antibody 212-10.7, while absorbed to the surface of a polystyrene microtiter assay plate, is capable of recognizing rPTHLP(1-87) or rPTHLP(1-141) when present in .human serum. Subsequently, the bound polypeptide may be recognized by a second antibody also specific for PTHLP. Although several of the monoclonal antibodies bind antigen simultaneously (i.e. they recognize different, independent epitopes) the greatest sensitivity was observed when the affinity-purified rabbit polyclonal antisera recognizing the trpE::PTHLP(19-87) fusion protein was employed. FIG. 4 shows the standard curves obtained with PTHLP(1-87) when either PBS-0.1% BSA, normal human serum, or an $E.\ coli$ lysate (trpE::K-ras$^{asp}$12) was used as diluent. It is apparent that the assay has a sensitivity of 1.25 ng/ml of PTHLP(1-87) in buffer or in serum, and that this method is free of artefacts due to nonspecific binding of irrelevent antigens. Further, FIG. 4 contains the response observed when an irrelevent MAb (MAb 528 which recognizes the human EGF receptor) is used as the capture immunoglobulin. Since no signal above background was observed it is apparent that the stringent conditions in the current protocol have eliminated ionic binding due to the high positive charge of PTHLP or any other irrelevent protein and that the signal observed with monoclonal 212-10.7 as capture antibody is due to a specific antibody-antigen interaction.

We have used this assay to detect PTHLP secreted into the media by cultured cell lines (FIG. 5). Conditioned media from the SKRC-1 cell line served as a positive control. This cell line has previously been shown to secrete PTHLP (19). SCaBER, a line derived from a squamous carcinoma of the bladder, was also found to secrete significant amounts of PTHLP although the absolute amount of PTHLP secreted by each cell line may depend on the growth conditions and the growth phase. None of the other cell lines tested secreted detectable levels of PTHLP. These included a normal human lung fibroblast (CCL-202), a normal mouse fibroblast (NIH 3T3), a squamous carcinoma from human lung (SK-MES-1), a squamous carcinoma from human tongue (SCC-15), an adenocarcinoma from human kidney (A498) and a human monocyte derived cell line (U937).

The combination of a sensitive immunometric assay for PTHLP and a cell line which secretes PTHLP allows the elucidation of the circulating form(s) of PTHLP. Of great importance is to compare the half-life of rPTHLP in human plasma to that in serum and to determine the effect of coagulation on PTHLP. Assay of plasma or serum, from nu/nu "nude" mice injected with cells known to produce PTHLP, using the two-site immunometric assay (which recognizes PTHLP(1-87) and larger species) and an assay for the amino terminal region of PTHLP (e.g. amino acids 1-34) should indicate whether circulating PTHLP species contain the majority of the amino-half of the polypeptide or if the circulating form is a smaller, amino-terminal containing fragment.

Inhibition of PTHLP Bioactivity Using MAbs

Despite the knowledge that the monoclonal antibodies described in this report do not recognize the amino-terminal region required for receptor binding, a preliminary experiment using the canine renal membrane adenylate cyclase assay indicated that binding by these MAbs does inhibit the ability of PTHLP(1-87) to stimulate the production of cAMP (Table 3). This result suggests that the MAbs can cause a conformational change in PTHLP or present a steric hindrance to the ligand-receptor interaction leading to a diminution of the polypeptide's bioactivity. Although complete inactivation has not yet been observed, one may obtain MAbs which can completely block the activity of PTHLP by binding the amino-terminal region directly or through an indirect mechanism involving a different epitope as hypothesized above. In addition, complete inactivation of PTHLP may not be necessary to alleviate the symptoms of HHM if these MAbs are used as therapeutic agents. In fact, complete inactivation may not even be desirable since the normal physiologic role of PTHLP is not known and the complete elimination of in vivo PTHLP activity may have adverse effects.

TABLE 3

Inhibition of Bioactivity by Monoclonal Antibodies

| MAb | % PTHLP (1-87) Activity Remaining | % PTH (1-84) Activity Remaining |
|---|---|---|
| 212-1 | 103[a] | N.D. |
| 212-2.4 | 86[a] | N.D. |
| 212-3 | 102[a] | N.D. |
| 212-4.4 | 73[a] | N.D. |
| 212-5 | 81[a] | N.D. |
| 212-6 | 116[a] | N.D. |
| 212-7 | 81[a] | N.D. |
| 212-8 | 80[a] | N.D. |
| 212-10.7 | 53[b] | 95[a] |
| 212-11 | 47[a] | N.D. |
| 212-13.13 | 78[a] | N.D. |
| 199-999 | 43[b] | 109[a] |
| 199-278 | 44[b] | 100[a] |
| 528 (a-hEGF receptor) | 85[c] | 100[a] |

[a]The data resulted from a single experiment
[b]The data resulted from 4 independent experiments
[c]The data resulted from 3 independent experiments
N.D.: Not determined Discussion The results described indicate that the immunological reagents have a high affinity, bind PTHLP with extreme specificity, and are capable of neutralizing its biological activity. Presently, there are no other monoclonal antibodies available which recognize PTHLP and the polyclonal sera which have been produced previously are incapable of sensitive detection of PTHLP(1-87) or PTHLP(1-141) and are unsuitable for use with complex biological samples such as sera. Thus, the unique nature of the approach to the production of PTHLP specific monoclonal and polyclonal antibodies, including the use of recombinant trpE::PTHLP fusion proteins as immunogens, which is described herein has led to the production of antibodies with immunological reactivities superior to those of previously developed PTHLP-specific antibodies.

These immunological reagents have permitted development of a highly sensitive and specific two-site immunometric assay for PTHLP in biological samples which will be useful for immunohistochemical analysis of the expression of PTHLP in tissues and tumors. Such immunoassays will be extremely valuable as research tools in both basic and clinical laboratories investigating the regulation of calcium metabolism in humans under normal conditions as well as pathological conditions such as HHM and possibly nonmalignant conditions such as osteoporosis.

It has also been demonstrated that certain of these antibodies are capable of inhibiting the biological activity of rPTHLP(1-87) in the canine renal membrane adenylate cyclase assay, a result which supports the proposition that the PTHLP-specific antibodies described herein are useful as therapeutic agents to alleviate the severe symptoms of HHM by neutralizing circulating PTHLP secreted by certain tumors.

REFERENCES

1. Albright, F. (1941) Case records of the Massachusetts General Hospital (Case 27461). N. Engl. J. Med. 225: 789-791.
2. Plimpton, C. H. and Gellhorn, A. (1956) Hypercalcemia in malignant disease without evidence of bone destruction. Amer. J. Med. 21: 750-759.
3. Connor, T. B., et al. (1956) The etiology of hypercalcemia associated with lung carcinoma, J. Clin. Invest. 35: 697-698.
4. Strewler, G. J. and Nissenson, R. A. (1987) Nonparathyroid Hypercalcemia, Adv. Intern. Med. 32: 235-258.
5. Stewart, A. F., et al., (1980) Biochemical evaluation of patients with cancer-associated hypercalcemia, New Eng. J. Med. 303: 1377-1383.
6. Godsall, J. W., et al., (1986) Nephrogenous cyclic AMP, adenylate cyclase-stimulating activity, and the Humoral Hypercalcemia of Malignancy, Recent Progress Hormone Res. 42: 705-750.
7. Stewart, A. F., et al., (1983) Identificaiton of adenylate cyclase-stimulating activity and cytochemical glucose-6-phosphate dehydrogenase stimulating activity in extracts of tumors from patients with humoral hypercalcemia of malignancy, Proc. Natl. Acad. Sci. U.S.A. 80: 1454-1458.
8. Burtis, W. J., et al., (1987) Identification of a novel 17,000 dalton parathyroid hormone-like adenylate cyclase-stimulating protein from a tumor associated with humoral hypercalcemia of malignancy, J. Biol. Chem. 262: 7151-7156.
9. Stewart, A. F., et al., (1987) N-terminal amino acid sequence of two novel tumor-derived adenylate cyclase-stimulating proteins: identification of parathyroid hormone-like and parathyroid hormone-unlike domains,. Biochem. Biophys. Res. Commun. 146: 672-678.
10. Rodan, S. B., et al., (1983) Factors associated with humoral hypercalcemia of malignancy stimulate adenylate cyclase in osteoblastic cells, J. Clin. Invest, 72: 1511-1515.
11. Strewler, G. J., et al., (1983) Human renal carcinoma cells produce hypercalcemia in the nude mouse and a novel protein recognized by parathyroid hormone receptors, J. Clin. Invest, 71: 769-774.
12. Nissenson, R. A., et al., (1985) Activation of the parathyroid hormone receptor-adenylate cyclase system in osteosarcoma cells by a human renal carcinoma factor. Cancer Res. 45: 5358-5363.

13. Merendino Jr., J. J., et al., (1986) A parathyroid hormone-like protein from cultured human keratinocytes, Science 231: 388–390.
14. Moseley, J. M., et al., (1987) Parathyroid hormone-related protein purified from a human lung cancer cell line, Proc. Natl. Acad. Sci. U.S.A. 84: 5048–5052.
15. Weir, E. C., et al., (1988) In vitro adenylate cyclase-stimulating activity predicts the occurrence of humoral hypercalemia of malignancy in nude mice, J.Clin. Invest. 81: 818–821.
16. Motokura, T., et al., (1988) Expression of parathyroid hormone-related protein in a human T cell lymphotrophic virus type 1-infected T cell line, Biochem. Biophys. Res. Commun, 154: 1182–1188.
17. Strewler, G. J., et al., (1987) Parathyroid hormone-like protein from human renal carcinoma cells: Structural and functional homology with parathyroid hormone, J. Clin. Invest. 80: 1803–1807.
18. Suva, L. J., et al., (1987) A parathyroid hormone-related protein implicated in malignant hypercalcemia: Cloning and expression, Science 237: 893–896.
19. Mangin, M., et al., (1988) Identification of a cDNA encoding a parathyroid hormone-like peptide from a human tumor associated with humoral hypercalcemia of malignancy, Proc. Natl. Acad. Sci. U.S.A. 85: 597–601.
20. Thiede, M., et al., Strewler, G. J., Nissenson, R. A., Rosenblatt, M. and Rodan, G. A. (1988) Human renal carcinoma expresses two mRNAs encoding a parathyroid hormone-like peptide: evidence for alternate splicing of the same gene, J. Bone. Min. Res. 3: (Suppl 1):579A.
21. Mangin, M., et al., (1988) Two distinct tumor derived, parathyroid hormone-like peptides result from alternative RNA processing, Endocrine Society Program and Abstracts, 70th Annual Meeting, New Orleans, Jun. 8–11, 1988, Abstract 21.
22. Horiuchi, N., et al., (1987) Similarity of synthetic peptide from human tumor to parathyroid hormone in vivo and in vitro, Science 238: 1566–1567.
23. Kemp, B. E., et al., (1987) Parathyroid hormone-related protein of malignancy: active synthetic fragments, Science 238: 1568–1570.
24. Nissenson, R. A., et al., (1988) Synthetic peptide comprising the amino-terminal sequence of a parathyroid hormone-like protein from human malignancies: Binding to parathyroid hormone receptors and activation of adenylate cyclase in bone cells and kidney, J. Biol. Chem. 263: 12866–12871.
25. Stewart, A. F., (1988) Synthetic human parathyroid hormone-like protein stimulates bone resorption and causes hypercalcemia in rats, J. Clin. Invest. 81: 596–600.
26. Thompson, D. D., et al., (1988) Direct action of the parathyroid hormone-like human hypercalcemic factor on bone, Proc. Natl. Acad. Sci. U.S.A. 85: 5673–5677.
27. Yates, A. J. P., et al., (1988) Effects of a synthetic peptide of a parathyroid hormone-related protein on calcium homeostasis, renal tubular calcium reabsorption, and bone metabolism in vivo and in vitro rodents, J. Clin. Invest. 81: 932–938.
28. Hammonds, R. G., et al., (1988) Activity of full-length PTH-related protein expressed in E. coli. J. Bone, Min. Res. 3 (Suppl): S69.
29. Wang, Y. N., et al., (1988). Parathyroid hormone-related protein in human plasma, Endocrine Society Program and Abstracts, 70th annual Meeting, New Orleans, Jun. 8–11, Abstract 308.
30. Dieckmann, C. L. and Tzagoloff, A. (1985) Assembly of the mitochondrial membrane system,. J. Biol. Chem. 260 1513.
31. Banaszuk, A. M., et al., (1983) An efficient method for the sequence analysis of oligodeoxyribonucleotides, Anal. Biochem. 128: 281.
32. Sanger, R. N., et al., (1977) DNA sequencing with chain-termination inhibitors, Proc. Natl. Acad, Sci. U.S.A. 74: 5463.
33. Nissenson, R. A., et al., (1981) Endogenous biologically active human parathyroid hormone: Measurement by a guanyl nucleotide-amplified renal adenylate cyclase assay, J. Clin. Endo. 52: 840–845.
34. Rosenblatt, M., et al., (1977) Parathyroid hormone inhibitors, J. Biol. Chem. 252: 5847–5851.
35. Stewart, A., et al., (1986) Frequency and partial characterization of adenylate cyclase-stimulatory activity in tumors associated with humoral hypercalcemia of malignancy, J. Bone Min. Res. 1: 267–276.
36. Levy, R. and Dilley, J. (1987) Rescue of immunoglobulin secretion from human neoplastic lymphoid cells by somatic cell hybridization, Proc. Natl. Acad. Sci. U.S.A. 75: 2411–2415.
37. Ibrahim, M. M., et al., (1982) Maintenance of normocalcemia by continuous infusion of synthetic bovine parathyroid hormone (1-34) in parathyroidectomized rats, Calcif. Tissue Int. 34: 553–557.

What is claimed is:

1. A monoclonal antibody which specifically binds to an epitope to which a monoclonal antibody produced by a hybridoma selected from the group consisting of 212-10.7 (ATCC No. HB9930), 199-999 (ATCC Accession No. HB9929), or 199-278 (ATCC Accession No. HB9931) binds.

2. A mouse monoclonal antibody of claim 1.

3. A monoclonal antibody of claim 1, wherein the epitope is within amino acids 19-87 of parathyroid hormone-like protein (PTHLP).

4. The antibody of claim 1 labeled with a detectable marker.

5. The antibody of claim 4, wherein the detectable marker is an enzyme, biotin, a fluorophore, a chromophore, a heavy metal, a paramagnetic isotope, or a radioisotope.

6. A monoclonal antibody of claim 1 bound to a solid support.

7. A monoclonal antibody which specifically binds to the epitope to which the monoclonal antibody produced by the hybridoma 199-999 (ATCC No. HB9929) binds.

8. The monoclonal antibody produced by the hybridoma 199-999 (ATCC No. HB9929).

9. Hybridoma 199-999 (ATCC No. HB9929).

10. A monoclonal antibody which specifically binds to the epitope to which the monoclonal antibody produced by the hybridoma 212-10.7 (ATCC No. HB9930) binds.

11. The monoclonal antibody produced by the hybridoma 212-10.7 (ATCC No. HB9930).

12. Hybridoma 212-10.7 (ATCC No. HB9930).

13. A monoclonal antibody which specifically binds to the epitope to which the monoclonal antibody produced by the hybridoma 199-278 (ATCC No. HB9931) binds.

14. The monoclonal antibody produced by the hybridomas 199-278 (ATCC No. HB9931).

15. Hybridoma 199-278 (ATCC No. HB9931).

* * * * *